United States Patent [19]
Chitwood

[11] Patent Number: 6,045,525
[45] Date of Patent: Apr. 4, 2000

[54] PNEUMATIC LUMBAR TRACTION DEVICE

[75] Inventor: Ralph M. Chitwood, Kalispell, Mont.

[73] Assignee: Glacier Cross, Inc., Kalispell, Mont.

[21] Appl. No.: 09/163,214

[22] Filed: Sep. 29, 1998

[51] Int. Cl.[7] ..................................................... A61F 5/00
[52] U.S. Cl. ................................ 602/36; 602/32; 602/38; 128/869
[58] Field of Search .................................... 128/869, 870, 128/871, 845, 846, 875, 877, 882; 602/32, 33, 34, 35, 13, 19; 606/241, 237, 242, 243, 244, 240; 242/147 K; 5/621–624, 643, 646–651

[56] References Cited

U.S. PATENT DOCUMENTS

| | | |
|---|---|---|
| Re. 32,791 | 11/1988 | Saunders . |
| 3,960,146 | 6/1976 | Albrecht . |
| 4,073,290 | 2/1978 | Farrar, Jr. . |
| 4,099,523 | 7/1978 | Lowrey . |
| 4,114,611 | 9/1978 | Lyle et al. ................................... 602/32 |
| 4,135,503 | 1/1979 | Romano . |
| 4,356,816 | 11/1982 | Granberg . |
| 4,466,427 | 8/1984 | Granberg . |
| 4,508,109 | 4/1985 | Saunders . |
| 4,627,423 | 12/1986 | Kampner . |
| 4,641,637 | 2/1987 | Rosen . |
| 4,664,101 | 5/1987 | Granberg . |
| 4,995,378 | 2/1991 | Dyer et al. . |
| 5,052,378 | 10/1991 | Chitwood . |
| 5,115,802 | 5/1992 | Dyer . |
| 5,181,904 | 1/1993 | Cook et al. ................................. 602/32 |
| 5,217,488 | 6/1993 | Wu .............................................. 602/32 |
| 5,478,307 | 12/1995 | Wang .......................................... 602/32 |
| 5,662,597 | 9/1997 | Chitwood ................................... 602/32 |
| 5,667,529 | 9/1997 | Butner . |

Primary Examiner—Kim M. Lee
Attorney, Agent, or Firm—Thomas R. Vigil

[57] ABSTRACT

The pneumatic lumbar traction device comprises two separable parts, namely an upper hollow shell and a lower plate or frame. The plate or frame has a pneumatically operated piston and cylinder mechanism located centrally thereof with a piston rod extending outwardly to engage a guided bar guided in a guideway mounted to the plate or frame. The guided bar extends outwardly of a foot end of the hollow shell and the plate or frame has an outer perimeter. The hollow shell has an inner perimeter which is sized to seat over and around the outer perimeter of the plate or frame, such that the outer perimeter of the plate or frame can bear against the inner perimeter of said hollow shell at a head end of the device when traction is placed on the lumbar region of a users back. The hollow shell has the foot end and a head end. The opening at the foot end allows the guided bar to extend therethrough. Further the hollow shell has an upper smooth surface on which a user will lie and a chest strap is fixed to the upper surface of the hollow shell. A pelvic traction belt is adapted to be received around the pelvic area of a user and has at least one strap extending outwardly toward a foot end of the device. And a T-bar, having a lower portion thereof adapted to be fixed to an outer end of the guided bar and an upper portion thereof adapted to hold at least one strap, extends from the pelvic traction belt.

18 Claims, 3 Drawing Sheets

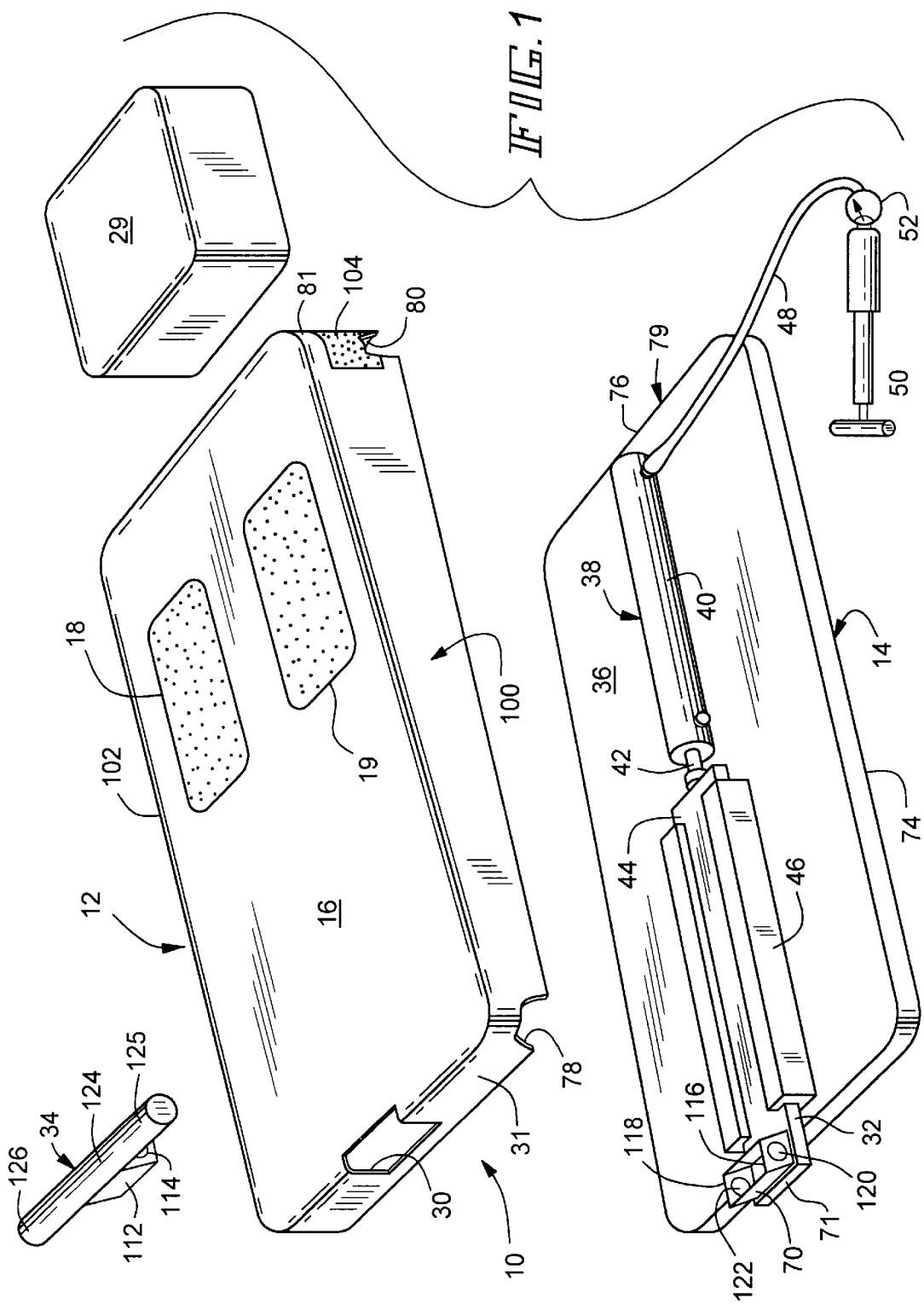

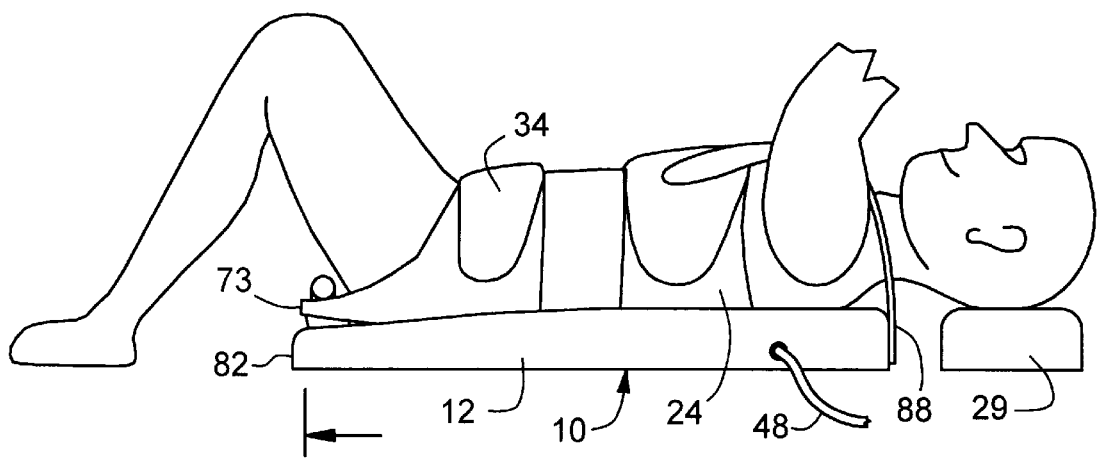
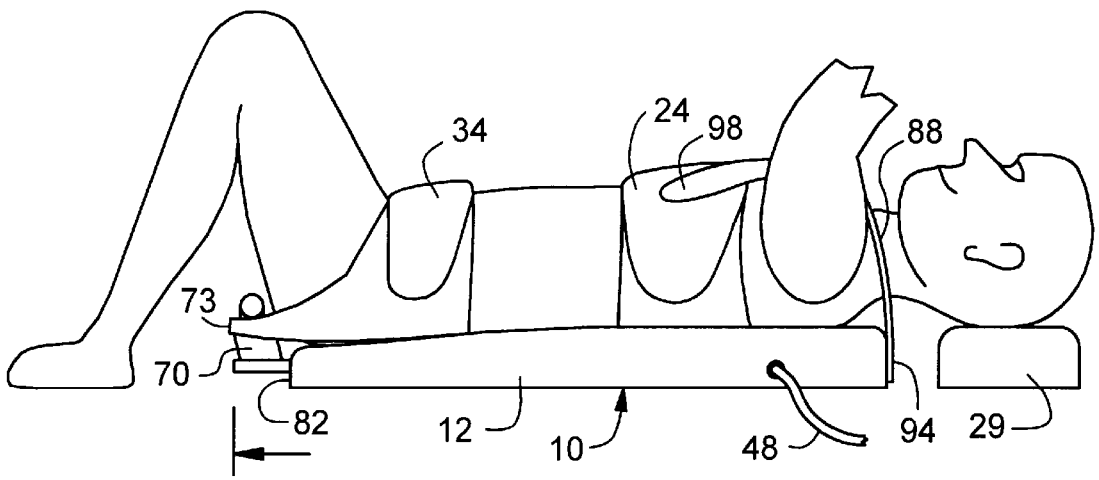

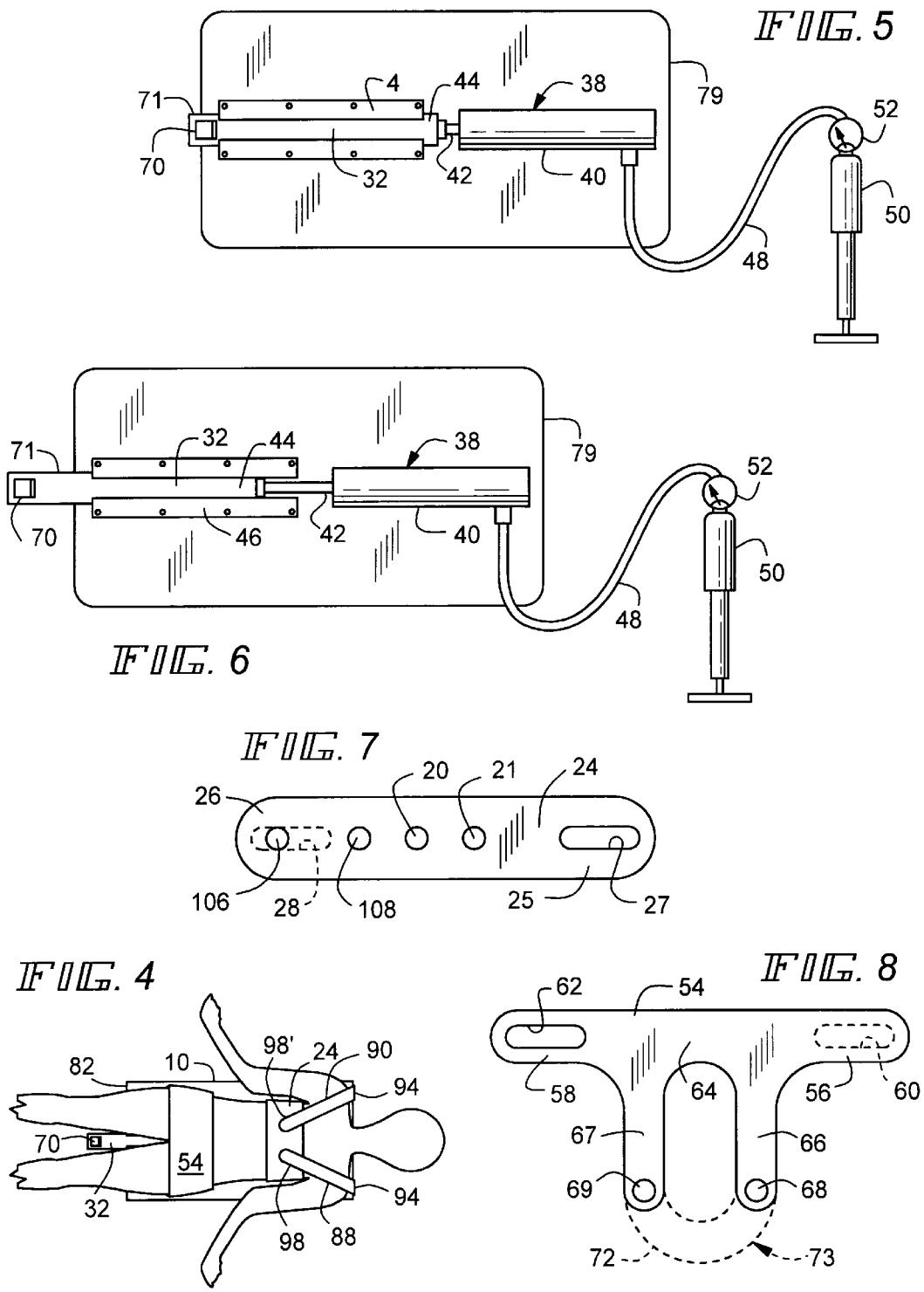

PNEUMATIC LUMBAR TRACTION DEVICE

BACKGROUND OF THE INVENTION

1. Field of the Invention

The present invention relates to a pneumatic lumbar traction device which can be placed on the floor or any other horizontal surface, such as a table, and the user thereof can strap himself or herself to the device and then, by pumping a hand pump, can cause a lower pelvic traction belt strapped around the pelvic area to be pulled outwardly from a foot end of the device with a chest strap holding the user to an upper surface of the device.

2. Description of the Prior Art

Heretofore various traction belts and traction devices have been proposed where a user can exert a stretching force on the lumbar area of the back. Examples of previously proposed traction belts and traction devices are disclosed in the following U.S. Pat. Nos.:

| U.S. Pat. No. | Patentee |
| --- | --- |
| 3,960,146 | Albrecht |
| 4,073,290 | Farrar, Jr. |
| 4,099,523 | Lowrey |
| 4,135,503 | Romano |
| 4,356,816 | Granberg |
| 4,466,427 | Granberg |
| 4,508,109 | Saunders |
| Re. 32,791 | Saunders |
| 4,627,423 | Kampner |
| 4,641,637 | Rosen |
| 4,664,101 | Granberg |
| 4,995,378 | Dyer et al. |
| 5,052,378 | Chitwood |
| 5,115,802 | Dyer |
| 5,667,529 | Butner |

Furthermore, a Saunders lumbar traction device sold under the trademark STx™ applies force via a hand-held pump which causes the lower half of the device to glide over a friction-free surface with the lower half of the user's body moving with the lower half of the device.

The Albrecht U.S. Pat. No. 3,960,146, the Farrar, Jr. U.S. Pat. No. 4,073,290, the Chitwood U.S. Pat. No. 5,052,378, and the Rosen U.S. Pat. No. 4,641,637 all disclose a traction belt with a lower strap for engaging an outer end of the piston or other mechanism for pulling the traction belt in a direction away from the torso of the person using the traction belt at a foot end of the device.

The Granberg U.S. Pat. Nos. 4,466,427 and 4,664,101 disclose a traction table for pelvic traction or cervical traction. The traction table utilizes a hydraulic system for a hydraulic piston cylinder located underneath the table.

As will be described in greater detail hereinafter, the pneumatic lumbar traction device of the present invention differs from the various devices disclosed in the prior art patents and literature described above by providing an upper hollow shell part for supporting a user's body and having, on an upper surface thereof, Velcro™ patches for holding a chest strap to the upper part, and a lower part having a framework or plate with a centrally located, pneumatically operated, piston and cylinder mechanism having a piston rod which extends out of a foot end of the device and which is adapted to engage a T-bar which is connectable to a pelvic traction belt received around the user's pelvic area, a hand pump being provided for moving the piston in the cylinder to extend the piston rod while the chest strap fixed to an upper surface of the upper part holds the user to the device.

SUMMARY OF THE INVENTION

According to the present invention there is provided a pneumatic lumbar traction device comprising: two separable parts, namely an upper hollow shell and a lower board, plate or frame. The plate or frame has a pneumatically operated piston and cylinder mechanism located centrally thereof with a piston rod extending outwardly to engage a guided bar guided in a guideway mounted to the plate or frame. The guided bar extends outwardly of a foot end of the hollow shell and the plate or frame having an outer perimeter. The hollow shell has an inner perimeter which is sized to seat over and around the outer perimeter of the plate or frame, such that the outer perimeter of the plate or frame can bear against the inner perimeter of said hollow shell at a head end of the device when traction is placed on the lumbar region of a users back. The hollow shell has the foot end and a head end, the opening at the foot end allowing the guided bar to extend therethrough. Further the hollow shell has an upper smooth surface on which a user will lie and a chest strap is fixed to the upper surface of the hollow shell. A pelvic traction belt is adapted to be received around the pelvic area of a user and has at least one strap extending outwardly toward a foot end of the device. And a T-bar, having a lower portion thereof adapted to be fixed to an outer end of the guided bar and an upper portion thereof adapted to hold at least one strap, extends from the pelvic traction belt.

BRIEF DESCRIPTION OF THE DRAWINGS

FIG. 1 is an exploded perspective view of the pneumatic lumbar traction device including an upper, hollow shell part and a lower plate part constructed according to the teachings of the present invention.

FIG. 2 is a side elevational view of the device shown in FIG. 1 with a user resting on the device.

FIG. 3 is a side elevational view of the device, similar to the view shown in FIG. 2, but showing straps of a pelvic traction belt connected to a traction bar and extending from a foot end of the device.

FIG. 4 is a top plan view of the user and the device shown in FIG. 3.

FIG. 5 is a top plan view of the lower plate part of the device which includes a plate mounting a pneumatic piston and cylinder mechanism, a guideway for a piston rod extending from the cylinder and an air pump.

FIG. 6 is a top plan view of a lower plate part of the device with the piston rod of the pneumatic piston and cylinder mechanism extended.

FIG. 7 is a bottom plan view of a chest strap shown in FIG. 4.

FIG. 8 is a top plan view of the pelvic traction belt shown in FIG. 4.

DESCRIPTION OF THE PREFERRED EMBODIMENT(S)

Referring now to the drawings in greater detail, there is illustrated in FIG. 1 a pneumatic lumbar traction device 10 constructed according to the teachings of the present invention. The device 10 includes an upper, hollow shell part 12 and a lower board, plate or framework part 14.

The upper, hollow shell part 12 is generally rectangular and constructed and arranged to fit over the lower plate part 14 and has an upper surface 16 which can be a slippery surface, such as by being coated with a lubricous material, such as Teflon™.

It is important to note that on the upper surface 16 there are provided two patches 18 and 19 of hook and loop material sold under the trademark Velcro™. The patches 18 and 19 are adapted to engage with patches 20 and 21 of hook and loop material (Velcro™) on the outside of a chest strap or belt 24 (FIG. 7) for holding the chest strap 24 to the upper surface 16 of the upper, hollow shell part 12. The chest strap 24 further has overlapping lower and upper strap end portions 25 and 26 which are fixed to each other by patches of hook and loop material 27 and 28.

The lumbar traction device 10 can also include a pillow 29, if desired, or such a pillow 29 can be provided by the user.

As shown, the upper, hollow shell part 12 has an opening 30 at a foot end 31 of the upper, hollow shell part 12 through which a generally rectangular-in-cross-section guided bar 32 can extend for connection to a T-bar 34.

The lower plate part 14 comprises a generally rectangularly shaped board, plate or frame 36 having centrally mounted thereon, a pneumatic piston and cylinder mechanism 38 comprising a cylinder 40 and a piston (hidden from view) which acts upon a piston rod 42 extending outwardly out of the piston and cylinder mechanism 38 for engagement with one end 44 of the guided bar 32.

A track or guideway 46 is mounted on the board or plate 14 for holding the guided bar 32 against lateral movement during use of the device 10.

Extending from the cylinder 40 is a tubing 48 which extends to a pump 50 and an air gauge 52. The pump 50 can be a hand operated pump, as shown, similar to a bicycle tire pump, or it can be a bulb type pump with a check valve, as is known in the art.

The pneumatic lumbar traction device 10 further includes a pelvic traction belt 54, as shown in FIG's. 4 and 8, including two lateral straps 56 and 58 which are adapted to be received around a person's pelvis and fixed together by means of mating patches 60 and 62 of hook and loop material which are commonly sold under the trademark Velcro™.

As shown in FIG. 8, the pelvic traction belt 54 has a central body portion 64. Then, extending from a lower side of the central body portion 64 of the pelvic traction belt 54 are two straps 66 and 67 which are adapted to be connected to the T-bar 34, by means of hole 68 and 69 or around the T-bar 34 and a projection 70 fixed to and extending upwardly from an outer end 71 of the guided bar 32. If desired, the straps 66, 68 can be integral with each through a bight portion 72 to form a strap loop 73, as shown in phantom in FIG. 8, which is received around the projection 70.

If desired, the outer surface of the pelvic traction belt 54 can be coated with or made from a lubricous material, such as polytetraflourethylene, commonly sold under the tradename Teflon™ to facilitate sliding of the user and the pelvic traction belt 54 on the upper surface 16 of the upper part 12.

It will be understood that the board or plate 14 has an outer perimeter 74 (FIG. 1) which fits within an inner perimeter 78 of the hollow shell part 12 such that an upper edge 76 at a head end 79 of the outer perimeter 74 of the board or plate 14 will bear against the inside of an upper wall 80 of the inner perimeter 78 of the hollow shell part 14 at a head end 81 of the hollow shell part 14 when air pressure is applied to the piston and cylinder mechanism 38 to cause the piston rod 42 to extend outwardly and force the guided bar 34 from a foot end 82 of the device 10 to pull the pelvic traction belt 54 away from the chest strap or belt 24 on the upper surface 16 of the hollow shell part 14.

In this way, a simple pneumatic lumbar traction device 10 is provided where a chest strap 24 is fixed to the upper surface 16 of the hollow shell part 14, such as with patches 18–21 of hook and loop material, as described above, or other fastening means, and the chest strap 24 can then be fastened tightly around the chest of a user. Then, with the user held to the upper hollow shell part 12 by the chest strap 24, the pelvic traction belt 54 can be pulled outwardly from the foot end 82 of the device 10 for stretching and placing traction on the lumbar area of the users back.

Desirably, the upper surface 16 is inclined slightly, 1 to 15 degrees, from the foot end 82 of the device 10 to a head end 86 of the device 10, as shown in FIG. 1, to facilitate sliding movement of the user on the upper surface 16.

Also it will be noted that the device 10 can include a pair of shoulder straps 88 and 90 each having a patch of hook and loop material at an upper end 94 of the strap 88 or 90 and a patch of hook and loop material at the other end 98 of each strap 88 or 90. Then, the head end 81 of the hollow shell part 14 in an area on each side of and adjacent a corner with one of two long side wall portions 100 and 102 of the hollow shell portion 16 has a patch of hook and loop material 104 which mates with the patch at the upper end 94 of one of the straps 88 or 90. Further the patches of hook and loop material at the end 98 are adapted to mate with one of two spaced patches 106 or 108 of hook and loop material on an outer surface of the upper strap portion 26 of the chest strap 24.

Further, as best shown in FIG. 1, the T-bar 34 has a wide lower portion 112 which has a hole 114 therethrough and the projection 70 is hollow, is sized to receive the portion 112 and has side walls 116 and 118 each having a hole 120 or 122 which mates with the hole 114 for receiving a pin, such as a clevis pin, that is releasably locked in place with a ring or cotter pin. The T-bar then has a rod shaped upper cross member 124 with outer end portions 125 and 126. The holes 68 and 69 in the straps 66 and 67 are then received over end portions 125 and 126 or the straps 66 and 68 are integral through the bight portion 72 and the strap loop 73 is received around the projection 70 beneath the end portions 125 and 126 as shown in FIGS. 2 and 3.

From the foregoing description, it will be apparent that the pneumatic lumbar traction device 10 of the present invention has a number of advantages, some of which have been described above and others which are inherent in the invention.

I claim:

1. A pneumatic lumbar traction device comprising:

two separable parts, namely an upper hollow shell and a lower board, plate or frame, said plate or frame having a pneumatically operated piston and cylinder mechanism located centrally thereof with a piston rod extending outwardly to engage a guided bar guided in a guideway mounted to said plate or frame, said guided bar extending outwardly of a foot end of said hollow shell and said plate or frame having an outer perimeter;

said hollow shell having an inner perimeter which is sized to seat over and around said outer perimeter of said plate or frame, such that said outer perimeter of said plate or frame can bear against said inner perimeter of said hollow shell at a head end of said device when traction is placed on the lumbar region of the user's back;

said hollow shell having said foot end with an end opening and a head end;

said end opening at said foot end allowing said guided bar to extend therethrough;

said hollow shell having an upper surface on which a user will lie during use;

a chest strap;

means for fixing said chest strap to said upper surface;

a pelvic traction belt adapted to be received around the pelvic area of a user and having at least one strap extending outwardly toward said foot end; and, a T-bar having a lower portion thereof adapted to be fixed to an outer end of said guided bar and having an upper portion thereof adapted to hold at least one strap extending from said pelvic traction belt.

2. The pneumatic lumbar traction device of claim 1 wherein said chest strap is releasably fixed to said upper surface of said hollow shell.

3. The pneumatic lumbar traction device of claim 1 wherein said fixing means comprise at least one patch of hook and loop material on said upper surface and at least one patch of hook and loop material on an outer surface of said chest strap for releasably engaging said patch of hook and loop material on said upper surface of said hollow shell.

4. The pneumatic lumbar traction device of claim 1 wherein said head end of said hollow shell is adapted to receive the back of the user and said device further includes a pillow separate from said upper and lower parts and adapted to be positioned under the user's head.

5. The pneumatic lumbar traction device of claim 1 including a hand pump coupled to said piston and cylinder mechanism for enabling a user to apply air pressure to the pneumatic piston and cylinder assembly to move said piston rod outwardly and thereby pull at least one strap of said pelvic traction belt toward the foot end of said device thereby to place traction with said pelvic traction belt on the lumbar region of the back of the user while the user is held by said chest strap to said upper surface of said hollow shell.

6. The pneumatic lumbar traction device of claim 5 wherein said hand pump includes an air gauge and is constructed similar to a bicycle tire pump.

7. The pneumatic lumbar traction device of claim 1 wherein said pelvic traction belt includes two laterally extending straps adapted to overlap each other and means for fixing the overlapping straps together.

8. The pneumatic lumbar traction device of claim 7 wherein said means for releasably attaching the overlapping straps together include a patch of hook and loop material on one surface of one strap and a mating patch of hook and loop material on another surface of the other strap.

9. The pneumatic lumbar traction device of claim 1 wherein said pelvic traction belt has two spaced apart straps which extend toward the user's feet and which are adapted to be received around the outer ends of a upper cross member of said T-bar.

10. The pneumatic lumbar traction device of claim 1 wherein said pelvic traction belt has a belt loop which extends toward the user's feet and which is adapted to be received beneath outer ends of said T-bar and around an upwardly extending projection fixed to and extending upwardly from said guided bar.

11. The pneumatic lumbar traction device of claim 1 wherein said T-bar has a lower portion with a hole therethrough for receiving a pin which also extends through a transverse hole in an outer end of said guide bar and an upper cross member of the T-bar adapted to be connected to two straps or a strap loop which extend or extends from said pelvic traction belt.

12. The pneumatic lumbar traction device of claim 1 wherein said chest strap includes first and second oppositely laterally extending straps which are adapted to be releasably fixed to each other around a chest of a user.

13. The pneumatic lumbar traction device of claim 12 wherein means for fixing said overlapping straps together include a patch of hook and loop material on one surface of one strap and a patch of hook and loop material on a mating surface of the other strap.

14. The pneumatic lumbar traction device of claim 1 wherein an outer end of said guided bar has a hollow projection fixed to and extending upwardly therefrom, said projection being sized to receive therein a wide lower base portion of said T-bar, said projection and said base portion having aligned holes therethrough in a direction transverse of said guided bar, and a pin being releasably received in and fixed in said aligned holes and a strap loop of said traction belt being received around said projection.

15. The pneumatic lumbar traction device of claim 1 wherein said hollow shell has a generally rectangular wall including opposite long portions, a foot portion and a head portion and has an upper wall portion.

16. The pneumatic lumbar traction device of claim 15 wherein upper wall portion of said hollow shell is inclined a small amount upwardly from said foot side wall portion to said head side wall portion.

17. The pneumatic lumbar traction device of claim 15 wherein said head side wall portion in an area on each side and adjacent a corner with one of said long side wall portions has a patch of hook and loop material and wherein said device further includes a pair of shoulder straps, each shoulder strap having a patch of hook and loop material on an inner surface thereof at each end thereof, one patch adapted to mate with one of said patches adjacent one of said corners and the other patch adapted to mate with one of two spaced patches of hook and loop material on an outer surface of said upper lateral strap of said chest strap.

18. The pneumatic lumbar traction device of claim 1 wherein said upper surface of said hollow shell is coated with a lubricous material.

* * * * *